United States Patent
Xia et al.

(10) Patent No.: US 11,987,850 B2
(45) Date of Patent: May 21, 2024

(54) UNIVERSAL PROBE, PRIMER-PROBE SET AND KIT

(71) Applicant: PILOT GENE TECHNOLOGY (HANGZHOU) CO., LTD., Zhejiang (CN)

(72) Inventors: Jiang Xia, Zhejiang (CN); Hao Yu, Zhejiang (CN)

(73) Assignee: PILOT GENE TECHNOLOGY (HANGZHOU) CO., LTD., Zhejiang (CN)

(*) Notice: Subject to any disclaimer, the term of this patent is extended or adjusted under 35 U.S.C. 154(b) by 0 days.

(21) Appl. No.: 18/326,300

(22) Filed: May 31, 2023

(65) Prior Publication Data
US 2024/0084405 A1 Mar. 14, 2024

Related U.S. Application Data

(63) Continuation of application No. PCT/CN2023/092551, filed on May 6, 2023.

(30) Foreign Application Priority Data

Aug. 31, 2022 (CN) .......................... 202211052186.6

(51) Int. Cl.
C12Q 1/68 (2018.01)
C12Q 1/689 (2018.01)
C12Q 1/6895 (2018.01)
C12Q 1/6844 (2018.01)

(52) U.S. Cl.
CPC ........... *C12Q 1/689* (2013.01); *C12Q 1/6895* (2013.01); *C12Q 1/6844* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 5,866,336 A | * | 2/1999 | Nazarenko | C12Q 1/6844 435/6.12 |
| 6,326,145 B1 | * | 12/2001 | Whitcombe | C12Q 1/6853 536/25.4 |
| 2008/0233572 A1 | | 9/2008 | Noble et al. | |

FOREIGN PATENT DOCUMENTS

| | | | | |
|---|---|---|---|---|
| CN | 103781908 A | | 5/2014 | |
| CN | 105734119 A | | 7/2016 | |
| CN | 110564824 A | * | 12/2019 | ........... C12Q 1/6851 |
| CN | 110564824 A | | 12/2019 | |
| CN | 110628940 A | * | 12/2019 | |
| CN | 111088378 A | * | 5/2020 | ........... C12Q 1/6851 |
| CN | 111593131 A | * | 8/2020 | |
| CN | 113584191 A | * | 11/2021 | |
| CN | 113584191 A | | 11/2021 | |
| CN | 113621727 A | | 11/2021 | |
| CN | 116064859 A | * | 5/2023 | |
| CN | 116064859 A | | 5/2023 | |

OTHER PUBLICATIONS

English translation of CN-110564824A, pub Dec. 13, 2019 (Year: 2019).*
English translation of CN-110628940A, pub Dec. 31, 2019 (Year: 2019).*
English translation of CN-111088378A, pub May 1, 2020 (Year: 2020).*
English translation of CN-111593131A, Aug. 28, 2020 (Year: 2020).*
English translation of CN-113584191A, pub Nov. 2, 2021 (Year: 2021).*
Afonina et al., 2002. Minor groove binder-conjugated DNA probes for quantitative DNA detection by hybridization-triggered fluorescence. Biotechniques, 32(4), pp. 940-949. (Year: 2002).*
Genbank Accession No. PP273433—Pseudomonas aeruginosa strain MIQ 16S ribosomal RNA gene, partial sequence (submitted Feb. 5, 2024, retrieved on Mar. 12, 2024 from http://www.ncbi.nlm.nih.gov/nuccore/PP273433). (Year: 2024).*
Genbank Accession No. CP041354 Pseudomonas aeruginosa strain AZPAE15042 chromosome, complete genome (submitted on Jun. 27, 2019, retrieved on Mar. 12, 2024 from http://www.ncbi.nlm.nih.gov/nuccore/CP041354). (Year: 2019).*
Marras, S.A., Russell Kramer, F. and Tyagi, S., 2003 Methods in Molecular Biology, vol. 212: Single Nucleotide Polymorphisms. Genotyping SNPs with molecular beacons. Single nucleotide polymorphisms: Methods and protocols, Humana Press pp. 111-128. (Year: 2003).*
Nazarenko et al., 1997. A closed tube format for amplification and detection of DNA based on energy transfer. Nucleic acids research, 25(12), pp. 2516-2521. (Year: 1997).*
International Search Report of Corresponding Application PCT/CN2023/092551, mailed Aug. 14, 2023; 6 pages.

* cited by examiner

*Primary Examiner* — Stephanie K Mummert
*Assistant Examiner* — Olayinka A Oyeyemi
(74) *Attorney, Agent, or Firm* — Cooper Legal Group, LLC

(57) ABSTRACT

The present application relates to a field of a biological detection technology, in particular, relates to a universal probe, a primer-probe set and a kit. The present application provides a universal probe, in which, from 5' end to 3' end, the universal probe sequentially comprises: quenching group-fragment A -fluorophore-fragment B-C3; the fragment A has a nucleotide sequence selected from a group consisting of SEQ ID NO:1-7; and the fragment B has a nucleotide sequence selected from a group consisting of SEQ ID NO:8-14. The present application further provide a primer-probe set, an application and the kit.

11 Claims, No Drawings
Specification includes a Sequence Listing.

SEQUENCE LISTING

```
Sequence total quantity: 102
SEQ ID NO: 1              moltype = DNA   length = 23
FEATURE                   Location/Qualifiers
source                    1..23
                          mol_type = other DNA
                          organism = synthetic construct
SEQUENCE: 1
agccccctca gggtccaggg ggc                                               23

SEQ ID NO: 2              moltype = DNA   length = 23
FEATURE                   Location/Qualifiers
source                    1..23
                          mol_type = other DNA
                          organism = synthetic construct
SEQUENCE: 2
aggcccctg ctacgtgggg gcc                                                23

SEQ ID NO: 3              moltype = DNA   length = 23
FEATURE                   Location/Qualifiers
source                    1..23
                          mol_type = other DNA
                          organism = synthetic construct
SEQUENCE: 3
agggcccctg actgccaggg ccc                                               23

SEQ ID NO: 4              moltype = DNA   length = 23
FEATURE                   Location/Qualifiers
source                    1..23
                          mol_type = other DNA
                          organism = synthetic construct
SEQUENCE: 4
aggggcccctg gcatgctggc ccc                                              23

SEQ ID NO: 5              moltype = DNA   length = 23
FEATURE                   Location/Qualifiers
source                    1..23
                          mol_type = other DNA
                          organism = synthetic construct
SEQUENCE: 5
aggggggccaa ggtccgagcc ccc                                              23

SEQ ID NO: 6              moltype = DNA   length = 23
FEATURE                   Location/Qualifiers
source                    1..23
                          mol_type = other DNA
                          organism = synthetic construct
SEQUENCE: 6
agggggggcga cgtcggtccc ccc                                              23

SEQ ID NO: 7              moltype = DNA   length = 23
FEATURE                   Location/Qualifiers
source                    1..23
                          mol_type = other DNA
                          organism = synthetic construct
SEQUENCE: 7
agccgggcga cgtcggtccc ggc                                               23

SEQ ID NO: 8              moltype = DNA   length = 28
FEATURE                   Location/Qualifiers
source                    1..28
                          mol_type = other DNA
                          organism = synthetic construct
SEQUENCE: 8
catgctgagg tgtagaccca tggattcc                                          28

SEQ ID NO: 9              moltype = DNA   length = 25
FEATURE                   Location/Qualifiers
source                    1..25
                          mol_type = other DNA
                          organism = synthetic construct
SEQUENCE: 9
catgctgtta ccaggcccc tctcc                                              25

SEQ ID NO: 10             moltype = DNA   length = 30
FEATURE                   Location/Qualifiers
source                    1..30
                          mol_type = other DNA
                          organism = synthetic construct
```

-continued

```
SEQUENCE: 10
catgctcatc ccaaaatatg ggctaacacc                                              30

SEQ ID NO: 11           moltype = DNA   length = 26
FEATURE                 Location/Qualifiers
source                  1..26
                        mol_type = other DNA
                        organism = synthetic construct
SEQUENCE: 11
catgctcgat ctcgaatcga agcacc                                                  26

SEQ ID NO: 12           moltype = DNA   length = 27
FEATURE                 Location/Qualifiers
source                  1..27
                        mol_type = other DNA
                        organism = synthetic construct
SEQUENCE: 12
catggaaatg ggtagacaaa gcaggcc                                                 27

SEQ ID NO: 13           moltype = DNA   length = 25
FEATURE                 Location/Qualifiers
source                  1..25
                        mol_type = other DNA
                        organism = synthetic construct
SEQUENCE: 13
catgctgtct gcaacacgaa gctcc                                                   25

SEQ ID NO: 14           moltype = DNA   length = 25
FEATURE                 Location/Qualifiers
source                  1..25
                        mol_type = other DNA
                        organism = synthetic construct
SEQUENCE: 14
catgggaaaa agagcttcgt gcagc                                                   25

SEQ ID NO: 15           moltype = DNA   length = 41
FEATURE                 Location/Qualifiers
source                  1..41
                        mol_type = other DNA
                        organism = synthetic construct
SEQUENCE: 15
gaatccatgg gtctacacct cagccttgac atgctgagaa c                                 41

SEQ ID NO: 16           moltype = DNA   length = 44
FEATURE                 Location/Qualifiers
source                  1..44
                        mol_type = other DNA
                        organism = synthetic construct
SEQUENCE: 16
gaatccatgg gtctacacct cagcaaggga gtaaagttaa tacc                              44

SEQ ID NO: 17           moltype = DNA   length = 43
FEATURE                 Location/Qualifiers
source                  1..43
                        mol_type = other DNA
                        organism = synthetic construct
SEQUENCE: 17
gaatccatgg gtctacacct cagcataacc tcatcgattg acg                               43

SEQ ID NO: 18           moltype = DNA   length = 42
FEATURE                 Location/Qualifiers
source                  1..42
                        mol_type = other DNA
                        organism = synthetic construct
SEQUENCE: 18
gaatccatgg gtctacacct cagcttgaca tactagaaac tt                                42

SEQ ID NO: 19           moltype = DNA   length = 39
FEATURE                 Location/Qualifiers
source                  1..39
                        mol_type = other DNA
                        organism = synthetic construct
SEQUENCE: 19
gagaggggc ctggtaacag catagagcct tccccttcg                                     39

SEQ ID NO: 20           moltype = DNA   length = 39
FEATURE                 Location/Qualifiers
source                  1..39
                        mol_type = other DNA
```

```
                             organism = synthetic construct
SEQUENCE: 20
gagaggggc ctggtaacag catagagctt ccccttcgg                              39

SEQ ID NO: 21           moltype = DNA   length = 37
FEATURE                 Location/Qualifiers
source                  1..37
                        mol_type = other DNA
                        organism = synthetic construct
SEQUENCE: 21
gagaggggc ctggtaacag cagagctttc ccttcgg                                37

SEQ ID NO: 22           moltype = DNA   length = 40
FEATURE                 Location/Qualifiers
source                  1..40
                        mol_type = other DNA
                        organism = synthetic construct
SEQUENCE: 22
gagaggggc ctggtaacag caaggtgttg tggttaataa                             40

SEQ ID NO: 23           moltype = DNA   length = 45
FEATURE                 Location/Qualifiers
source                  1..45
                        mol_type = other DNA
                        organism = synthetic construct
SEQUENCE: 23
gtgttagccc atattttggg atgagcctgt tatcccaaya caaac                      45

SEQ ID NO: 24           moltype = DNA   length = 42
FEATURE                 Location/Qualifiers
source                  1..42
                        mol_type = other DNA
                        organism = synthetic construct
SEQUENCE: 24
gtgttagccc atattttggg atgagcacta ccagcagatg cg                         42

SEQ ID NO: 25           moltype = DNA   length = 46
FEATURE                 Location/Qualifiers
source                  1..46
                        mol_type = other DNA
                        organism = synthetic construct
SEQUENCE: 25
gtgttagccc atattttggg atgagcatta gtatcggaag aactca                     46

SEQ ID NO: 26           moltype = DNA   length = 49
FEATURE                 Location/Qualifiers
source                  1..49
                        mol_type = other DNA
                        organism = synthetic construct
SEQUENCE: 26
gtgttagccc atattttggg atgagcagta tgtattcttt aacacgttg                  49

SEQ ID NO: 27           moltype = DNA   length = 36
FEATURE                 Location/Qualifiers
source                  1..36
                        mol_type = other DNA
                        organism = synthetic construct
SEQUENCE: 27
gtgcttcgat tcgagatcga gccgctgcgg ctagac                                36

SEQ ID NO: 28           moltype = DNA   length = 35
FEATURE                 Location/Qualifiers
source                  1..35
                        mol_type = other DNA
                        organism = synthetic construct
SEQUENCE: 28
gtgcttcgat tcgagatcga gccggtcgcg ctggc                                 35

SEQ ID NO: 29           moltype = DNA   length = 40
FEATURE                 Location/Qualifiers
source                  1..40
                        mol_type = other DNA
                        organism = synthetic construct
SEQUENCE: 29
gtgcttcgat tcgagatcga gatttgggcg tggttaagga                            40

SEQ ID NO: 30           moltype = DNA   length = 34
FEATURE                 Location/Qualifiers
source                  1..34
```

```
                          mol_type = other DNA
                          organism = synthetic construct
SEQUENCE: 30
gtgcttcgat tcgagatcaa gagtgatgcg tctc                                      34

SEQ ID NO: 31             moltype = DNA   length = 38
FEATURE                   Location/Qualifiers
source                    1..38
                          mol_type = other DNA
                          organism = synthetic construct
SEQUENCE: 31
gcctgctttg tctacccatt tccagcagag gagcgagg                                  38

SEQ ID NO: 32             moltype = DNA   length = 34
FEATURE                   Location/Qualifiers
source                    1..34
                          mol_type = other DNA
                          organism = synthetic construct
SEQUENCE: 32
gcctgctttg tctacccaga gaatacgaaa ctcg                                      34

SEQ ID NO: 33             moltype = DNA   length = 42
FEATURE                   Location/Qualifiers
source                    1..42
                          mol_type = other DNA
                          organism = synthetic construct
SEQUENCE: 33
gcctgctttg tctacccatt tgaaccaata tacatcggaa ta                             42

SEQ ID NO: 34             moltype = DNA   length = 44
FEATURE                   Location/Qualifiers
source                    1..44
                          mol_type = other DNA
                          organism = synthetic construct
SEQUENCE: 34
gagcttcgtg ttgcagacag catgttaaag aagatggtat gtgg                           44

SEQ ID NO: 35             moltype = DNA   length = 40
FEATURE                   Location/Qualifiers
source                    1..40
                          mol_type = other DNA
                          organism = synthetic construct
SEQUENCE: 35
gagcttcgtg ttgcagacag cctttttataa agcacaaatc                               40

SEQ ID NO: 36             moltype = DNA   length = 43
FEATURE                   Location/Qualifiers
source                    1..43
                          mol_type = other DNA
                          organism = synthetic construct
SEQUENCE: 36
ctgcacgaag ctcttttttcc cgcgacggat ctacgtcaca gcg                           43

SEQ ID NO: 37             moltype = DNA   length = 20
FEATURE                   Location/Qualifiers
source                    1..20
                          mol_type = other DNA
                          organism = synthetic construct
SEQUENCE: 37
gcaacgcgaa gaaccttacc                                                      20

SEQ ID NO: 38             moltype = DNA   length = 19
FEATURE                   Location/Qualifiers
source                    1..19
                          mol_type = other DNA
                          organism = synthetic construct
SEQUENCE: 38
gttcccgaag gcaccaatc                                                       19

SEQ ID NO: 39             moltype = DNA   length = 21
FEATURE                   Location/Qualifiers
source                    1..21
                          mol_type = other DNA
                          organism = synthetic construct
SEQUENCE: 39
ggccttcggg ttgtaaagta c                                                    21

SEQ ID NO: 40             moltype = DNA   length = 21
FEATURE                   Location/Qualifiers
```

```
source                  1..21
                        mol_type = other DNA
                        organism = synthetic construct
SEQUENCE: 40
tcttctgcgg gtaacgtcaa t                                              21

SEQ ID NO: 41           moltype = DNA   length = 18
FEATURE                 Location/Qualifiers
source                  1..18
                        mol_type = other DNA
                        organism = synthetic construct
SEQUENCE: 41
agcctgatgc agccatgc                                                  18

SEQ ID NO: 42           moltype = DNA   length = 20
FEATURE                 Location/Qualifiers
source                  1..20
                        mol_type = other DNA
                        organism = synthetic construct
SEQUENCE: 42
ttagccggtg cttcttctgc                                                20

SEQ ID NO: 43           moltype = DNA   length = 20
FEATURE                 Location/Qualifiers
source                  1..20
                        mol_type = other DNA
                        organism = synthetic construct
SEQUENCE: 43
gcaacgcgaa gaaccttacc                                                20

SEQ ID NO: 44           moltype = DNA   length = 19
FEATURE                 Location/Qualifiers
source                  1..19
                        mol_type = other DNA
                        organism = synthetic construct
SEQUENCE: 44
gttcccgaag gcaccaatc                                                 19

SEQ ID NO: 45           moltype = DNA   length = 20
FEATURE                 Location/Qualifiers
source                  1..20
                        mol_type = other DNA
                        organism = synthetic construct
SEQUENCE: 45
gcaacgcgaa gaaccttacc                                                20

SEQ ID NO: 46           moltype = DNA   length = 21
FEATURE                 Location/Qualifiers
source                  1..21
                        mol_type = other DNA
                        organism = synthetic construct
SEQUENCE: 46
catgcaccac ctgtcacttt g                                              21

SEQ ID NO: 47           moltype = DNA   length = 20
FEATURE                 Location/Qualifiers
source                  1..20
                        mol_type = other DNA
                        organism = synthetic construct
SEQUENCE: 47
gcaacgcgaa gaaccttacc                                                20

SEQ ID NO: 48           moltype = DNA   length = 21
FEATURE                 Location/Qualifiers
source                  1..21
                        mol_type = other DNA
                        organism = synthetic construct
SEQUENCE: 48
catgcaccac ctgtcacttt g                                              21

SEQ ID NO: 49           moltype = DNA   length = 24
FEATURE                 Location/Qualifiers
source                  1..24
                        mol_type = other DNA
                        organism = synthetic construct
SEQUENCE: 49
ggtggagcat gtggtttaat tcga                                           24

SEQ ID NO: 50           moltype = DNA   length = 21
```

```
FEATURE          Location/Qualifiers
source           1..21
                 mol_type = other DNA
                 organism = synthetic construct
SEQUENCE: 50
ctcacgacac gagctgacga c                                          21

SEQ ID NO: 51    moltype = DNA  length = 19
FEATURE          Location/Qualifiers
source           1..19
                 mol_type = other DNA
                 organism = synthetic construct
SEQUENCE: 51
tcctacggga ggcagcagt                                             19

SEQ ID NO: 52    moltype = DNA  length = 19
FEATURE          Location/Qualifiers
source           1..19
                 mol_type = other DNA
                 organism = synthetic construct
SEQUENCE: 52
ctgctggcac ggagttagc                                             19

SEQ ID NO: 53    moltype = DNA  length = 21
FEATURE          Location/Qualifiers
source           1..21
                 mol_type = other DNA
                 organism = synthetic construct
SEQUENCE: 53
tgcccaacag caactrsaag t                                          21

SEQ ID NO: 54    moltype = DNA  length = 23
FEATURE          Location/Qualifiers
source           1..23
                 mol_type = other DNA
                 organism = synthetic construct
SEQUENCE: 54
gaagccattt gttgtgatgt ttg                                        23

SEQ ID NO: 55    moltype = DNA  length = 25
FEATURE          Location/Qualifiers
source           1..25
                 mol_type = other DNA
                 organism = synthetic construct
SEQUENCE: 55
gagtttcttc gacaacgggt actac                                      25

SEQ ID NO: 56    moltype = DNA  length = 17
FEATURE          Location/Qualifiers
source           1..17
                 mol_type = other DNA
                 organism = synthetic construct
SEQUENCE: 56
tcctccggca ccacatg                                               17

SEQ ID NO: 57    moltype = DNA  length = 22
FEATURE          Location/Qualifiers
source           1..22
                 mol_type = other DNA
                 organism = synthetic construct
SEQUENCE: 57
tgtggcgtca ttgtgtaaca aa                                         22

SEQ ID NO: 58    moltype = DNA  length = 23
FEATURE          Location/Qualifiers
source           1..23
                 mol_type = other DNA
                 organism = synthetic construct
SEQUENCE: 58
attgtgttgt ttcaccgatg ttg                                        23

SEQ ID NO: 59    moltype = DNA  length = 22
FEATURE          Location/Qualifiers
source           1..22
                 mol_type = other DNA
                 organism = synthetic construct
SEQUENCE: 59
catccattgg ttgattttc ca                                          22
```

| | | |
|---|---|---|
| SEQ ID NO: 60<br>FEATURE<br>source | moltype = DNA   length = 23<br>Location/Qualifiers<br>1..23<br>mol_type = other DNA<br>organism = synthetic construct | |
| SEQUENCE: 60<br>tggatcgaca aaagaaaaa gga | | 23 |
| SEQ ID NO: 61<br>FEATURE<br>source | moltype = DNA   length = 20<br>Location/Qualifiers<br>1..20<br>mol_type = other DNA<br>organism = synthetic construct | |
| SEQUENCE: 61<br>ggcgcctaac aaggatgaca | | 20 |
| SEQ ID NO: 62<br>FEATURE<br>source | moltype = DNA   length = 18<br>Location/Qualifiers<br>1..18<br>mol_type = other DNA<br>organism = synthetic construct | |
| SEQUENCE: 62<br>gacgcccaat ccctcgag | | 18 |
| SEQ ID NO: 63<br>FEATURE<br>source | moltype = DNA   length = 22<br>Location/Qualifiers<br>1..22<br>mol_type = other DNA<br>organism = synthetic construct | |
| SEQUENCE: 63<br>ctggatcaag caggagatca ac | | 22 |
| SEQ ID NO: 64<br>FEATURE<br>source | moltype = DNA   length = 19<br>Location/Qualifiers<br>1..19<br>mol_type = other DNA<br>organism = synthetic construct | |
| SEQUENCE: 64<br>cgcccatctt gtcctgatg | | 19 |
| SEQ ID NO: 65<br>FEATURE<br>source | moltype = DNA   length = 20<br>Location/Qualifiers<br>1..20<br>mol_type = other DNA<br>organism = synthetic construct | |
| SEQUENCE: 65<br>cccaatagct tcatcgccct | | 20 |
| SEQ ID NO: 66<br>FEATURE<br>source | moltype = DNA   length = 24<br>Location/Qualifiers<br>1..24<br>mol_type = other DNA<br>organism = synthetic construct | |
| SEQUENCE: 66<br>gtccatccca cttaaagact tggt | | 24 |
| SEQ ID NO: 67<br>FEATURE<br>source | moltype = DNA   length = 23<br>Location/Qualifiers<br>1..23<br>mol_type = other DNA<br>organism = synthetic construct | |
| SEQUENCE: 67<br>gcaaaactgg ttgttccarg tca | | 23 |
| SEQ ID NO: 68<br>FEATURE<br>source | moltype = DNA   length = 22<br>Location/Qualifiers<br>1..22<br>mol_type = other DNA<br>organism = synthetic construct | |
| SEQUENCE: 68<br>aayccttaa ccgcctgctc ta | | 22 |
| SEQ ID NO: 69<br>FEATURE<br>source | moltype = DNA   length = 17<br>Location/Qualifiers<br>1..17<br>mol_type = other DNA<br>organism = synthetic construct | |
| SEQUENCE: 69<br>ccgttcccgc agacctt | | 17 |

-continued

| | | |
|---|---|---|
| SEQ ID NO: 70 | moltype = DNA length = 22 | |
| FEATURE | Location/Qualifiers | |
| source | 1..22 | |
| | mol_type = other DNA | |
| | organism = synthetic construct | |
| SEQUENCE: 70 | | |
| tttttgccg tttcctgtat cc | | 22 |

| | | |
|---|---|---|
| SEQ ID NO: 71 | moltype = DNA length = 23 | |
| FEATURE | Location/Qualifiers | |
| source | 1..23 | |
| | mol_type = other DNA | |
| | organism = synthetic construct | |
| SEQUENCE: 71 | | |
| catggtctgc ttgtcatgaa aga | | 23 |

| | | |
|---|---|---|
| SEQ ID NO: 72 | moltype = DNA length = 20 | |
| FEATURE | Location/Qualifiers | |
| source | 1..20 | |
| | mol_type = other DNA | |
| | organism = synthetic construct | |
| SEQUENCE: 72 | | |
| gggaaagcca cgtcaatacg | | 20 |

| | | |
|---|---|---|
| SEQ ID NO: 73 | moltype = DNA length = 23 | |
| FEATURE | Location/Qualifiers | |
| source | 1..23 | |
| | mol_type = other DNA | |
| | organism = synthetic construct | |
| SEQUENCE: 73 | | |
| gcagagattg ccaacaacat tga | | 23 |

| | | |
|---|---|---|
| SEQ ID NO: 74 | moltype = DNA length = 19 | |
| FEATURE | Location/Qualifiers | |
| source | 1..19 | |
| | mol_type = other DNA | |
| | organism = synthetic construct | |
| SEQUENCE: 74 | | |
| gcatgttttc caaacgcca | | 19 |

| | | |
|---|---|---|
| SEQ ID NO: 75 | moltype = DNA length = 24 | |
| FEATURE | Location/Qualifiers | |
| source | 1..24 | |
| | mol_type = other DNA | |
| | organism = synthetic construct | |
| SEQUENCE: 75 | | |
| aactacggta acattgatcg caac | | 24 |

| | | |
|---|---|---|
| SEQ ID NO: 76 | moltype = DNA length = 23 | |
| FEATURE | Location/Qualifiers | |
| source | 1..23 | |
| | mol_type = other DNA | |
| | organism = synthetic construct | |
| SEQUENCE: 76 | | |
| gcattcctgg aataatgacg cta | | 23 |

| | | |
|---|---|---|
| SEQ ID NO: 77 | moltype = DNA length = 21 | |
| FEATURE | Location/Qualifiers | |
| source | 1..21 | |
| | mol_type = other DNA | |
| | organism = synthetic construct | |
| SEQUENCE: 77 | | |
| cggtgaaaat atcccgagtg a | | 21 |

| | | |
|---|---|---|
| SEQ ID NO: 78 | moltype = DNA length = 25 | |
| FEATURE | Location/Qualifiers | |
| source | 1..25 | |
| | mol_type = other DNA | |
| | organism = synthetic construct | |
| SEQUENCE: 78 | | |
| ggccatatcc tgaatctgct aataa | | 25 |

| | | |
|---|---|---|
| SEQ ID NO: 79 | moltype = DNA length = 21 | |
| FEATURE | Location/Qualifiers | |
| source | 1..21 | |
| | mol_type = other DNA | |
| | organism = synthetic construct | |
| SEQUENCE: 79 | | | gcttcttgtg gagctcgaca a                                                     21

SEQ ID NO: 80           moltype = DNA   length = 21
FEATURE                 Location/Qualifiers
source                  1..21
                        mol_type = other DNA
                        organism = synthetic construct SEQUENCE: 80
ccgtcagcaa cttcgttttc a                                                     21

SEQ ID NO: 81           moltype = DNA   length = 18
FEATURE                 Location/Qualifiers
source                  1..18
                        mol_type = other DNA
                        organism = synthetic construct SEQUENCE: 81
ccttgacatg ctgagaac                                                         18

SEQ ID NO: 82           moltype = DNA   length = 20
FEATURE                 Location/Qualifiers
source                  1..20
                        mol_type = other DNA
                        organism = synthetic construct SEQUENCE: 82
aaggagtaa agttaatacc                                                        20

SEQ ID NO: 83           moltype = DNA   length = 18
FEATURE                 Location/Qualifiers
source                  1..18
                        mol_type = other DNA
                        organism = synthetic construct SEQUENCE: 83
taacctcatc gattgacg                                                         18

SEQ ID NO: 84           moltype = DNA   length = 20
FEATURE                 Location/Qualifiers
source                  1..20
                        mol_type = other DNA
                        organism = synthetic construct SEQUENCE: 84
ccttgacata ctagaaactt                                                       20

SEQ ID NO: 85           moltype = DNA   length = 17
FEATURE                 Location/Qualifiers
source                  1..17
                        mol_type = other DNA
                        organism = synthetic construct SEQUENCE: 85
tagagccttc cccttcg                                                          17

SEQ ID NO: 86           moltype = DNA   length = 18
FEATURE                 Location/Qualifiers
source                  1..18
                        mol_type = other DNA
                        organism = synthetic construct SEQUENCE: 86
atagagcttc cccttcgg                                                         18

SEQ ID NO: 87           moltype = DNA   length = 16
FEATURE                 Location/Qualifiers
source                  1..16
                        mol_type = other DNA
                        organism = synthetic construct SEQUENCE: 87
agagctttcc cttcgg                                                           16

SEQ ID NO: 88           moltype = DNA   length = 19
FEATURE                 Location/Qualifiers
source                  1..19
                        mol_type = other DNA
                        organism = synthetic construct SEQUENCE: 88
aaggtgttgt ggttaataa                                                        19

SEQ ID NO: 89           moltype = DNA   length = 20
FEATURE                 Location/Qualifiers
source                  1..20
                        mol_type = other DNA
                        organism = synthetic construct

```
SEQUENCE: 89
cctgttatcc caayacaaac                                                    20

SEQ ID NO: 90           moltype = DNA   length = 16
FEATURE                 Location/Qualifiers
source                  1..16
                        mol_type = other DNA
                        organism = synthetic construct
SEQUENCE: 90
actaccagca gatgcg                                                        16

SEQ ID NO: 91           moltype = DNA   length = 19
FEATURE                 Location/Qualifiers
source                  1..19
                        mol_type = other DNA
                        organism = synthetic construct
SEQUENCE: 91
ttagtatcgg aagaactca                                                     19

SEQ ID NO: 92           moltype = DNA   length = 24
FEATURE                 Location/Qualifiers
source                  1..24
                        mol_type = other DNA
                        organism = synthetic construct
SEQUENCE: 92
cagtatgtat tctttaacac gttg                                               24

SEQ ID NO: 93           moltype = DNA   length = 16
FEATURE                 Location/Qualifiers
source                  1..16
                        mol_type = other DNA
                        organism = synthetic construct
SEQUENCE: 93
gccgctgcgg ctagac                                                        16

SEQ ID NO: 94           moltype = DNA   length = 15
FEATURE                 Location/Qualifiers
source                  1..15
                        mol_type = other DNA
                        organism = synthetic construct
SEQUENCE: 94
gccggtcgcg ctggc                                                         15

SEQ ID NO: 95           moltype = DNA   length = 20
FEATURE                 Location/Qualifiers
source                  1..20
                        mol_type = other DNA
                        organism = synthetic construct
SEQUENCE: 95
gatttgggcg tggttaagga                                                    20

SEQ ID NO: 96           moltype = DNA   length = 17
FEATURE                 Location/Qualifiers
source                  1..17
                        mol_type = other DNA
                        organism = synthetic construct
SEQUENCE: 96
caagagtgat gcgtctc                                                       17

SEQ ID NO: 97           moltype = DNA   length = 16
FEATURE                 Location/Qualifiers
source                  1..16
                        mol_type = other DNA
                        organism = synthetic construct
SEQUENCE: 97
cagcagagga gcgagg                                                        16

SEQ ID NO: 98           moltype = DNA   length = 17
FEATURE                 Location/Qualifiers
source                  1..17
                        mol_type = other DNA
                        organism = synthetic construct
SEQUENCE: 98
agagaatacg aaactcg                                                       17

SEQ ID NO: 99           moltype = DNA   length = 22
FEATURE                 Location/Qualifiers
source                  1..22
                        mol_type = other DNA
```

```
                        organism = synthetic construct
SEQUENCE: 99
tgaaccaata tacatcggaa ta                                                    22

SEQ ID NO: 100          moltype = DNA  length = 22
FEATURE                 Location/Qualifiers
source                  1..22
                        mol_type = other DNA
                        organism = synthetic construct
SEQUENCE: 100
tgttaaagaa gatggtatgt gg                                                    22

SEQ ID NO: 101          moltype = DNA  length = 20
FEATURE                 Location/Qualifiers
source                  1..20
                        mol_type = other DNA
                        organism = synthetic construct
SEQUENCE: 101
ccttttataa agcacaaatc                                                       20

SEQ ID NO: 102          moltype = DNA  length = 23
FEATURE                 Location/Qualifiers
source                  1..23
                        mol_type = other DNA
                        organism = synthetic construct
SEQUENCE: 102
cgcgacggat ctacgtcaca gcg                                                   23
```

UNIVERSAL PROBE, PRIMER-PROBE SET AND KIT

CROSS-REFERENCE TO RELATED APPLICATION

This application is a continuation of PCT application serial no. PCT/CN2023/092551, filed on May 6, 2023, which claims the priority and benefit of Chinese patent application serial no. 202211052186.6, filed on Aug. 31, 2022. The entireties of PCT application serial no. PCT/CN2023/092551 and Chinese patent application serial no. 202211052186.6 are hereby incorporated by reference herein and made a part of this specification.

REFERENCE TO AN ELECTRONIC SEQUENCE LISTING

The contents of the electronic sequence listing (SequenceListing.xml; Size: 91,085 bytes; and Date of Creation: May 31, 2023) is herein incorporated by reference.

TECHNICAL FIELD

The present application relates to a field of a biological detection technology, in particular, relates to a universal probe, a primer-probe set and a kit.

BACKGROUND ART

A pathogenic microorganism is a microorganism that can cause an infectious disease or even a communicable disease after invading a human body. Common pathogenic microorganisms include prion, bacterium, mycoplasma, chlamydia, rickettsia, fungi, spirochete and virus. After repetitive exposure to some chemotherapeutic drugs, a reactivity of these pathogenic microorganisms continues to decrease, so that finally the pathogenic microorganisms can resist the drug without being killed or inhibited, and thus develop a tolerance to drugs, that is, a drug tolerance or drug resistance. A resistant gene is a nucleotide sequence encoding a drug resistance property, and is located on a chromosome of the bacterium or a plasmid outside the chromosomal. If the pathogenic microorganisms develop the drug resistance, an efficacy is commonly reduced or completely lost, which directly affect a therapeutic effect against the disease. Thus, establishing a systematic, efficient, and fast detection method for identifying a nucleic acid of a plurality of pathogenic microorganisms and resistant genes can effectively promote the development of the medical industry.

At present, a conventional detection method of nucleic acids of the pathogenic microorganisms and resistant genes mainly adopts a real-time quantitative PCR (qPCR), including a fluorescent dye method (SYBR Green I method is a representative) and a fluorescent probe method (TaqMan method is the representative). The SYBR Green I method is widely used due to advantages such as convenient use and low price, but a biggest disadvantage thereof is a lack of a specificity, that is, a dye can be combined with any dsDNA, which affects an accuracy of a quantitative result. Different from the fluorescent dye method, the TaqMan method detection involves an addition of a fluorescent probe, which works through fluorescence resonance energy transfer (FRET), and has a high specificity and suitability for multiplex qPCR. However, a traditional TaqMan probe technology usually requires one probe for each of the targets. However, when detecting multiple targets in one fluorescence channel, if there are too many probes labeled with a same fluorescence, it will lead to a high background signal and decreased contrast, resulting in difficult signal interpretation difficult and limited number of targets that can be detected.

SUMMARY

In view of this, a technical problem to be solved by the present application is to provide a primer-probe set and a kit containing the primer-probe for a digital PCR detection of a plurality of pathogenic microorganisms and resistant genes. The present application provides a digital PCR platform based on a 7-color fluorescence channel and in combination with multiplex digital PCR technology to achieve a coverage of multiple bacterial strains or drug resistance sites for each species.

The present application provides a universal probe structure, from 5' end to 3' end, the universal probe sequentially including: quenching group-fragment A-fluorophore-fragment B-C3.

In some embodiments, the fragment A has a nucleotide sequence selected from a group consisting of SEQ ID NO:1-7.

the fragment B has a nucleotide sequence selected from a group consisting of SEQ ID NO:8-14.

In some embodiments, from 5' end to 3' end, the universal probe sequentially includes one selected from a group consisting of:
  quenching group-fragment A having a nucleotide sequence of SEQ ID NO:1-fluorophore-fragment B-C3 having a nucleotide sequence of SEQ ID NO:8;
  quenching group-fragment A having a nucleotide sequence of SEQ ID NO:2-fluorophore-fragment B-C3 having a nucleotide sequence of SEQ ID NO:9;
  quenching group-fragment A having a nucleotide sequence of SEQ ID NO:3-fluorophore-fragment B-C3 having a nucleotide sequence of SEQ ID NO:10;
  quenching group-fragment A having a nucleotide sequence of SEQ ID NO:4-fluorophore-fragment B-C3 having a nucleotide sequence of SEQ ID NO:11;
  quenching group-fragment A having a nucleotide sequence of SEQ ID NO:5-fluorophore-fragment B-C3 having a nucleotide sequence of SEQ ID NO:12;
  quenching group-fragment A having a nucleotide sequence of SEQ ID NO:6-fluorophore-fragment B-C3 having a nucleotide sequence of SEQ ID NO:13; and
  quenching group-fragment A having a nucleotide sequence of SEQ ID NO:7-fluorophore-fragment B-C3 having a nucleotide sequence of SEQ ID NO:14.

The fluorophore of the universal probe described in the present application is selected from a group consisting of FAM, VIC, ROX, CY5, A425, CY5.5 and CY7; and the quenching group is selected from a group consisting of BHQ1, BHQ2 and BHQ3.

In some embodiments, the fluorophore A425 of the universal probe is fluorophore ATT0425.

In some embodiments, from 5' end to 3' end, the universal probe sequentially includes one selected from a group consisting of:
  BHQ1-fragment A having a nucleotide sequence of SEQ ID NO:1-dT-FAM-fragment B-C3 having a nucleotide sequence of SEQ ID NO:8;
  BHQ1-fragment A having a nucleotide sequence of SEQ ID NO:2-dT-VIC-fragment B-C3 having a nucleotide sequence of SEQ ID NO:9;

BHQ2-fragment A having a nucleotide sequence of SEQ ID NO:3-dT-ROX-fragment B-C3 having a nucleotide sequence of SEQ ID NO:10;

BHQ2-fragment A having a nucleotide sequence of SEQ ID NO:4-dT-CY5-fragment B-C3 having a nucleotide sequence of SEQ ID NO:11;

BHQ1-fragment A having a nucleotide sequence of SEQ ID NO:5-dT-A425-fragment B-C3 having a nucleotide sequence of SEQ ID NO:12;

BHQ3-fragment A having a nucleotide sequence of SEQ ID NO:6-dT-CY5.5 -fragment B-C3 having a nucleotide sequence of SEQ ID NO:13; and BHQ3-fragment A having a nucleotide sequence of SEQ ID NO:7-dT-CY7-fragment B-C3 having a nucleotide sequence of SEQ ID NO:14.

In the present application, the universal probe is in cooperation with a single-modified fluorescence-free probe. In particular, the single-modified fluorescence-free probe is specifically combined with an amplification product, and the universal probe is hybridized with a hydrolyzed fragment of the single-modified fluorescence-free probe to generate a fluorescent signal for a detection purpose.

The present application further provides a primer-probe set for detecting one selected from a group consisting of the pathogenic microorganism and the resistant gene, including the universal probe described in the present application.

The primer-probe set provided in the present application further includes a specific primer pair targeting the pathogenic microorganism and the resistant gene.

In particular, the pathogenic microorganism includes one selected from a group consisting of *Pseudomonas aeruginosa, Escherichia coli, Klebsiella pneumoniae, Acinetobacter baumannii, Staphylococcus aureus, Enterococcus faecium, Enterococcus faecalis, Enterobacter cloacae, Candida albicans, Candida glabrata, Candida parapsilosis* and *Candida tropicalis;* the resistant gene includes one selected from a group consisting of carbapenem resistant KPC gene, carbapenem resistant NDM gene, carbapenem resistant OXA48 gene, carbapenem resistant IMP gene, vancomycin resistant vanA gene, vancomycin resistant vanB gene, vancomycin resistant vanM gene, methicillin resistant mecA gene and methicillin resistant mecC gene.

Specifically, a primer pair targeting the *Pseudomonas aeruginosa* has a nucleotide sequence selected from a group consisting of SEQ ID NO:37-38;

a primer pair targeting the *Escherichia coli* has a nucleotide sequence selected from a group consisting of SEQ ID NO:39-40;

a primer pair targeting the *Klebsiella pneumoniae* has a nucleotide sequence selected from a group consisting of SEQ ID NO:41-42;

a primer pair targeting the *Acinetobacter baumannii* has a nucleotide sequence selected from a group consisting of SEQ ID NO:43-44;

a primer pair targeting the *Staphylococcus aureus* has a nucleotide sequence selected from a group consisting of SEQ ID NO:45-46;

a primer pair targeting the *Enterococcus faecium* has a nucleotide sequence selected from a group consisting of SEQ ID NO:47-48;

a primer pair targeting the *Enterococcus faecalis* has a nucleotide sequence selected from a group consisting of SEQ ID NO:49-50;

a primer pair targeting the *Enterobacter cloacae* has a nucleotide sequence selected from a group consisting of SEQ ID NO:51-52;

a primer pair targeting the *Candida albicans* has a nucleotide sequence selected from a group consisting of SEQ ID NO:53-54;

a primer pair targeting the *Candida glabrata* has a nucleotide sequence selected from a group consisting of SEQ ID NO:55-56;

a primer pair targeting the *Candida parapsilosis* has a nucleotide sequence selected from a group consisting of SEQ ID NO:57-58;

a primer pair targeting the *Candida tropicalis* has a nucleotide sequence selected from a group consisting of SEQ ID NO:59-60;

a primer pair targeting the carbapenem resistant KPC gene has a nucleotide sequence selected from a group consisting of SEQ ID NO:61-62;

a primer pair targeting the carbapenem resistant NDM gene has a nucleotide sequence selected from a group consisting of SEQ ID NO:63-64;

a primer pair targeting the carbapenem resistant OXA48 gene has a nucleotide sequence selected from a group consisting of SEQ ID NO:65-66;

a primer pair targeting the carbapenem resistant IMP gene has a nucleotide sequence selected from a group consisting of SEQ ID NO:67-68;

a primer pair targeting the vancomycin resistant vanA gene has a nucleotide sequence selected from a group consisting of SEQ ID NO:69-70;

a primer pair targeting the vancomycin resistant vanB gene has a nucleotide sequence selected from a group consisting of SEQ ID NO:71-72;

a primer pair targeting the vancomycin resistant vanM gene has a nucleotide sequence selected from a group consisting of SEQ ID NO:73-74;

a primer pair targeting the methicillin resistant mecA gene has a nucleotide sequence selected from a group consisting of SEQ ID NO:75-76; and, a primer pair targeting the methicillin resistant mecC gene has a nucleotide sequence selected from a group consisting of SEQ ID NO:77-78.

The primer-probe set provided in the present application further includes the single-modified fluorescence-free probe, a nucleotide sequence of the single-modified fluorescence-free probe is reversely complementary to a nucleotide sequence of the fragment B in the universal probe, and 3' end of the single-modified fluorescence-free probe is labeled with the quenching group. In particular, the quenching group is selected from a group consisting of MGB, BHQ1, BHQ2 and BHQ3.

Specifically, a single-modified fluorescence-free probe targeting the *Pseudomonas aeruginosa* has a nucleotide sequence as shown in SEQ ID NO:15, and 3' end is labeled with the MGB quenching group;

a single-modified fluorescence-free probe targeting the *Escherichia coli* has a nucleotide sequence as shown in SEQ ID NO:16, and 3' end is labeled with the MGB quenching group;

a single-modified fluorescence-free probe targeting the *Klebsiella pneumoniae* has a nucleotide sequence as shown in SEQ ID NO:17, and 3' end is labeled with the MGB quenching group;

a single-modified fluorescence-free probe targeting the *Acinetobacter baumannii* has a nucleotide sequence as shown in SEQ ID NO:18, and 3' end is labeled with the MGB quenching group;

a single-modified fluorescence-free probe targeting the *Staphylococcus aureus* has a nucleotide sequence as shown in SEQ ID NO:19, and 3' end is labeled with the MGB quenching group;

a single-modified fluorescence-free probe targeting the *Enterococcus faecium* has a nucleotide sequence as shown in SEQ ID NO:20, and 3' end is labeled with the MGB quenching group;

a single-modified fluorescence-free probe targeting the *Enterococcus faecalis* has a nucleotide sequence as shown in SEQ ID NO:21, and 3' end is labeled with the MGB quenching group;

a single-modified fluorescence-free probe targeting the *Enterobacter cloacae* has a nucleotide sequence as shown in SEQ ID NO:22, and 3' end is labeled with the MGB quenching group;

a single-modified fluorescence-free probe targeting the *Candida albicans* has a nucleotide sequence as shown in SEQ ID NO:23, and 3' end is labeled with the MGB quenching group;

a single-modified fluorescence-free probe targeting the *Candida glabrata* has a nucleotide sequence as shown in SEQ ID NO:24, and 3' end is labeled with the MGB quenching group;

a single-modified fluorescence-free probe targeting the *Candida parapsilosis* has a nucleotide sequence as shown in SEQ ID NO:25, and 3' end is labeled with the MGB quenching group;

a single-modified fluorescence-free probe targeting the *Candida tropicalis* has a nucleotide sequence as shown in SEQ ID NO:26, and 3' end is labeled with the MGB quenching group;

a single-modified fluorescence-free probe targeting the carbapenem resistant KPC gene has a nucleotide sequence as shown in SEQ ID NO:27, and 3' end is labeled with the MGB quenching group;

a single-modified fluorescence-free probe targeting the carbapenem resistant NDM gene has a nucleotide sequence as shown in SEQ ID NO:28, and 3' end is labeled with the BHQ2 quenching group;

a single-modified fluorescence-free probe targeting the carbapenem resistant OXA48 gene has a nucleotide sequence as shown in SEQ ID NO:29, and 3' end is labeled with the MGB quenching group;

a single-modified fluorescence-free probe targeting the carbapenem resistant IMP gene has a nucleotide sequence as shown in SEQ ID NO:30, and 3' end is labeled with the MGB quenching group;

a single-modified fluorescence-free probe targeting the vancomycin resistant vanA gene has a nucleotide sequence as shown in SEQ ID NO:31, and 3' end is labeled with the BHQ1 quenching group;

a single-modified fluorescence-free probe targeting the vancomycin resistant vanB gene has a nucleotide sequence as shown in SEQ ID NO:32, and 3' end is labeled with the BHQ1 quenching group;

a single-modified fluorescence-free probe targeting the vancomycin resistant vanM gene has a nucleotide sequence as shown in SEQ ID NO:33, and 3' end is labeled with the BHQ1 quenching group;

a single-modified fluorescence-free probe targeting the methicillin resistant mecA gene has a nucleotide sequence as shown in SEQ ID NO:34, and 3' end is labeled with the BHQ2 quenching group;

a single-modified fluorescence-free probe targeting the methicillin resistant mecC gene has a nucleotide sequence as shown in SEQ ID NO:35, and 3' end is labeled with the MGB quenching group.

The present application further provides an application of the universal probe or the primer-probe set in a preparation of digital PCR detection reagents for a plurality of pathogenic microorganisms and resistant genes.

The present application further provides a kit for detecting one selected from a group consisting of a plurality of pathogenic microorganisms and resistant genes, including one selected from a group consisting of the universal probe or the primer-probe set described in the present application.

The kit provided in the present application further includes a combination of a primer and a probe for an internal control gene, having the following sequences: IC-UP7: ctgcacgaagctcttttcccgcgacggatctacgtcacagcg (SEQ ID NO:36); IC-P: cgcgacggatctacgtcacagcg (SEQ ID NO:102); IC-F: gcttcttgtggagctcgacaa (SEQ ID NO:79); IC-R: ccgtcagcaacttcgttttca (SEQ ID NO:80).

The present application further provides a multiplex digital PCR detection method for a plurality of pathogenic microorganisms and resistant genes, utilizing the primer-probe set or the kit of the present application for detection.

The detection method based on a multiplex digital PCR platform includes the following steps:

(1) a nucleic acid of a sample to be tested is extracted;
(2) multiplex digital PCR amplification system is configured;
(3) an amplification program is run: 95° C. 5 min, (95° C. 15 s, 60° C. 1 min)×40;
(4) a result is output.

By using the primer-probe of the present application, a joint detection of 12 pathogenic microorganisms and 9 resistant genes can be achieved. In particular, the pathogenic microorganisms includes one selected from a group consisting of *Pseudomonas aeruginosa*, *Escherichia coli*, *Klebsiella pneumoniae*, *Acinetobacter baumannii*, *Staphylococcus aureus*, *Enterococcus faecium*, *Enterococcus faecalis*, *Enterobacter cloacae*, *Candida albicans*, *Candida glabrata*, *Candida parapsilosis* and *Candida tropicalis*; and the resistant genes include one selected from a group consisting of carbapenem resistant KPC gene, carbapenem resistant NDM gene, carbapenem resistant OXA48 gene, carbapenem resistant IMP gene, vancomycin resistant vanA gene, vancomycin resistant vanB gene, vancomycin resistant vanM gene, methicillin resistant mecA gene and methicillin resistant mecC gene.

For conservative regions of 12 pathogenic microorganisms and 9 resistant genes, the present application specifically designs 42 primers, 7 universal probes containing different fluorophores and 21 specific single-modified fluorescence-free probes in total. The universal probe is cooperated with a single-modified probe to generate the fluorescent signal, which can be used to detect whether the sample contains *Pseudomonas aeruginosa*, *Escherichia coli*, *Klebsiella pneumoniae*, *Acinetobacter baumannii*, *Staphylococcus aureus*, *Enterococcus faecium*, *Enterococcus faecalis*, *Enterobacter cloacae*, *Candida albicans*, *Candida glabrata*, *Candida parapsilosis* or *Candida tropicalis* in the sample, and detect whether the sample contains a site of carbapenem resistant KPC gene, carbapenem resistant NDM gene, carbapenem resistant OXA48 gene, carbapenem resistant IMP gene, vancomycin resistant vanA gene, vancomycin resistant vanB gene, vancomycin resistant vanM gene, methicillin resistant mecA gene or methicillin resistant mecC gene.

The present application adopts a single amplification system with a conventional double-modified probe and a multiplex amplification system with a cooperation of the universal probe and the single-modified probe, and the detection results of the two systems are consistent with each other, which ensures a feasibility of designing the universal probe containing different fluorophores for a target gene and combining them with the specific single-modified fluorescence-free probe to conduct the multiplex digital PCR.

DETAILED DESCRIPTION

The present application provides a primer-probe set and a kit thereof for a digital PCR detection of a plurality of pathogenic microorganisms and resistant genes, and those skilled in the art can appropriately improve a process parameter by learning from a content of the present application. It should be noted that, all similar replacements and modifications are apparent to those skilled in the art and are considered to fall within a scope of the present invention. A method and an application of the present application have been described through a preferred embodiment, and it is obvious that a relevant personnel can make modifications or appropriate changes and combinations of the method and application without departing from the content, spirit and scope of the present application to achieve and apply a technology of the present application.

Test materials used in the present application are all common commercially available and can be purchased in the market.

The present application is further described below in combination with examples.

EXAMPLE 1

Design of the Primer-Probe Set of the Present Application

A sequence of the primer-probe set involved in this example is shown in Table 1.

In particular, UP1-UP7 represents 7 universal probes with different colors. F represents an upstream primer, R represents a downstream primer, and P represents the probe. For example, TL-F represents an upstream primer of the *Pseudomonas aeruginosa*, TL-R represents a downstream primer of the *Pseudomonas aeruginosa*, TL-P represents a conventional double-modified probe of the *Pseudomonas aeruginosa*, and TL-UP1 represents the specific single-modified fluorescence-free probe of the *Pseudomonas aeruginosa*.

TABLE 1

| Name | Number | Sequence | 5' modification | 3' modification |
|---|---|---|---|---|
| universal probe | fragment A | Agcccccctcagggtccaggggc (SEQ ID NO: 1) | BHQ1 | |
| universal probe | fragment A | aggcccctgctacgtgggggcc (SEQ ID NO: 2) | BHQ1 | |
| universal probe | fragment A | agggcccctgactgccagggccc (SEQ ID NO: 3) | BHQ2 | |
| universal probe | fragment A | aggggccctggcatgctggcccc (SEQ ID NO: 4) | BHQ2 | |
| universal probe | fragment A | aggggccaaggtccgagccccc (SEQ ID NO: 5) | BHQ1 | |
| universal probe | fragment A | aggggggcgacgtcggtcccccc (SEQ ID NO: 6) | BHQ3 | |
| universal probe | fragment A | agccgggcgacgtcggtcccggc (SEQ ID NO: 7) | BHQ3 | |
| universal probe | fragment B | catgctgaggtgtagacccatggattcc (SEQ ID NO: 8) | | C3 |
| universal probe | fragment B | catgctgttaccaggcccctctcc (SEQ ID NO: 9) | | C3 |
| universal probe | fragment B | catgctcatcccaaaatatgggctaacacc (SEQ ID NO: 10) | | C3 |
| universal probe | fragment B | catgctcgatctcgaatcgaagcacc (SEQ ID NO: 11) | | C3 |
| universal probe | fragment B | catggaaatgggtagacaaagcaggcc (SEQ ID NO: 12) | | C3 |
| universal probe | fragment B | catgctgtctgcaacacgaagctcc (SEQ ID NO: 13) | | C3 |
| universal probe | fragment B | catgggaaaaagagcttcgtgcagc (SEQ ID NO: 14) | | C3 |
| *pseudomonas aeruginosa* | TL-UP1 | gaatccatgggtctacacctcagccttgacatgctgagaac (SEQ ID NO: 15) | | MGB |
| *escherichia coli* | DC-UP1 | gaatccatgggtctacacctcagcaagggagtaaagttaatac c (SEQ ID NO: 16) | | MGB |
| *klebsiella pneumoniae* | FK-UP1 | gaatccatgggtctacacctcagcataacctcatcgattgacg (SEQ ID NO: 17) | | MGB |
| *acinetobacter baumannii* | BM-UP1 | gaatccatgggtctacacctcagcttgacatactagaaactt (SEQ ID NO: 18) | | MGB |
| *staphylococcus aureus* | JP-UP2 | gagaggggcctggtaacagcatagagccttcccttcg (SEQ ID NO: 19) | | MGB |

TABLE 1-continued

| Name | Number | Sequence | 5' modification | 3' modification |
|---|---|---|---|---|
| enterococcus faecium | SC-UP2 | gagaggggccctggtaacagcatagagcttccccttcgg (SEQ ID NO: 20) | | MGB |
| enterococcus faecalis | FC-UP2 | gagaggggccctggtaacagcagagctttcccttcgg (SEQ ID NO: 21) | | MGB |
| enterobacter cloacae | YG-UP2 | gagaggggccctggtaacagcaaggtgttgtggttaataa (SEQ ID NO: 22) | | MGB |
| candida albicans | BS-UP3 | gtgttagcccatattttgggatgagcctgttatcccaayacaaac (SEQ ID NO: 23) | | MGB |
| candida glabrata | GH-UP3 | gtgttagcccatattttgggatgagcactaccagcagatgcg (SEQ ID NO: 24) | | MGB |
| candida parapsilosis | JPH-UP3 | gtgttagcccatattttgggatgagcattagtatcggaagaactca (SEQ ID NO: 25) | | MGB |
| candida parapsilosis | RD-UP3 | gtgttagcccatattttgggatgagcagtatgtattctttaacacgttg (SEQ ID NO: 26) | | MGB |
| carbapenem resistant KPC | KPC-UP4 | gtgcttcgattcgagatcgagccgctgcggctagac (SEQ ID NO: 27) | | MGB |
| carbapenem resistant NDM | NDM-UP4 | gtgcttcgattcgagatcgagccggtcgcgctggc (SEQ ID NO: 28) | | BHQ2 |
| carbapenem resistant OXA48 | OXA48-UP4 | gtgcttcgattcgagatcgagatttgggcgtggttaagga (SEQ ID NO: 29) | | MGB |
| carbapenem resistant IMP | IMP-UP4 | gtgcttcgattcgagatcaagagtgatgcgtctc (SEQ ID NO: 30) | | MGB |
| vancomycin resistant vanA | vanA-UP5 | gcctgctttgtctacccatttccagcagaggagcgagg (SEQ ID NO: 31) | | BHQ1 |
| vancomycin resistant vanB | VANB-UP5 | gcctgctttgtctacccagagaatacgaaactcg (SEQ ID NO: 32) | | BHQ1 |
| vancomycin resistant vanM | VANM-UP5 | gcctgctttgtctacccatttgaaccaatatacatcggaata (SEQ ID NO: 33) | | BHQ1 |
| methicillin resistant mecA | MECA-UP6 | gagcttcgtgttgcagacagcatgttaaagaagatggtatgtgg (SEQ ID NO: 34) | | BHQ2 |
| methicillin resistant mecC | mecC-UP6 | gagcttcgtgttgcagacagcctttataaagcacaaatc (SEQ ID NO: 35) | | MGB |
| exogenous internal control | IC-UP7 | ctgcacgaagctctttttcccgcgacggatctacgtcacagcg (SEQ ID NO: 36) | | BHQ3 |
| pseudomonas aeruginosa | TL-F | gcaacgcgaagaaccttacc (SEQ ID NO: 37) | | |
| pseudomonas aeruginosa | TL-R | gttcccgaaggcaccaatc (SEQ ID NO: 38) | | |
| escherichia coli | DC-F | ggccttcgggttgtaaagtac (SEQ ID NO: 39) | | |
| escherichia coli | DC-R | tcttctgcgggtaacgtcaat (SEQ ID NO: 40) | | |
| klebsiella pneumoniae | FK-F | agcctgatgcagccatgc (SEQ ID NO: 41) | | |
| klebsiella pneumoniae | FK-R | ttagccggtgcttcttctgc (SEQ ID NO: 42) | | |
| acinetobacter baumannii | BM-F | gcaacgcgaagaaccttacc (SEQ ID NO: 43) | | |
| acinetobacter baumannii | BM-R | gttcccgaaggcaccaatc (SEQ ID NO: 44) | | |

TABLE 1-continued

| Name | Number | Sequence | 5' modification | 3' modification |
|---|---|---|---|---|
| staphylococcus aureus | JP-F | gcaacgcgaagaaccttacc (SEQ ID NO: 45) | | |
| staphylococcus aureus | JP-R | catgcaccacctgtcactttg (SEQ ID NO: 46) | | |
| enterococcus faecium | SC-F | gcaacgcgaagaaccttacc (SEQ ID NO: 47) | | |
| enterococcus faecium | SC-R | catgcaccacctgtcactttg (SEQ ID NO: 48) | | |
| enterococcus faecalis | FC-F | ggtggagcatgtggtttaattcga (SEQ ID NO: 49) | | |
| enterococcus faecalis | FC-R | ctcacgacacgagctgacgac (SEQ ID NO: 50) | | |
| enterobacter cloacae | YG-F | tcctacgggaggcagcagt (SEQ ID NO: 51) | | |
| enterobacter cloacae | YG-R | ctgctggcacggagttagc (SEQ ID NO: 52) | | |
| candida albicans | BS-F | tgcccaacagcaactrsaagt (SEQ ID NO: 53) | | |
| candida albicans | BS-R | gaagccatttgttgtgatgtttg (SEQ ID NO: 54) | | |
| candida glabrata | GH-F | gagtttcttcgacaacgggtactac (SEQ ID NO: 55) | | |
| candida glabrata | GH-R | tcctccggcaccacatg (SEQ ID NO: 56) | | |
| candida parapsilosis | JPH-F | tgtggcgtcattgtgtaacaaa (SEQ ID NO: 57) | | |
| candida parapsilosis | JPH-R | attgtgttgtttcaccgatgttg (SEQ ID NO: 58) | | |
| candida tropicalis | RD-F | catccattggttgattttttcca (SEQ ID NO: 59) | | |
| candida tropicalis | RD-R | tggatcgacaaaaagaaaaagga (SEQ ID NO: 60) | | |
| carbapenem resistant KPC | KPC-F | ggcgcctaacaaggatgaca (SEQ ID NO: 61) | | |
| carbapenem resistant KPC | KPC-R | gacgcccaatccctcgag (SEQ ID NO: 62) | | |
| carbapenem resistant NDM | NDM-F | ctggatcaagcaggagatcaac (SEQ ID NO: 63) | | |
| carbapenem resistant NDM | NDM-R | cgcccatcttgtcctgatg (SEQ ID NO: 64) | | |
| carbapenem resistant OXA48 | OXA48-F | cccaatagcttcatcgccct (SEQ ID NO: 65) | | |
| carbapenem resistant OXA48 | OXA48-R | gtccatcccacttaaagacttggt (SEQ ID NO: 66) | | |
| carbapenem resistant IMP | IMP-F | gcaaaactggttgttccargtca (SEQ ID NO: 67) | | |
| carbapenem resistant IMP | IMP-R | aaycctttaaccgcctgctcta (SEQ ID NO: 68) | | |
| vancomycin resistant vanA | vanA-F | ccgttcccgcagaccctt (SEQ ID NO: 69) | | |

TABLE 1-continued

| Name | Number | Sequence | 5' modification | 3' modification |
|---|---|---|---|---|
| vancomycin resistant vanA | vanA-R | tttttttgccgtttcctgtatcc (SEQ ID NO: 70) | | |
| vancomycin resistant vanB | vanB-F | catggtctgcttgtcatgaaaga (SEQ ID NO: 71) | | |
| vancomycin resistant vanB | vanB-R | gggaaagccacgtcaatacg (SEQ ID NO: 72) | | |
| vancomycin resistant vanM | vanM-F | gcagagattgccaacaacattga (SEQ ID NO: 73) | | |
| vancomycin resistant vanM | vanM-R | gcatgttttccaaacgcca (SEQ ID NO: 74) | | |
| methicillin resistant mecA | mecA-F | aactacggtaacattgatcgcaac (SEQ ID NO: 75) | | |
| methicillin resistant mecA | mecA-R | gcattcctggaataatgacgcta (SEQ ID NO: 76) | | |
| methicillin resistant mecC | mecC-F | cggtgaaaatatcccgagtga (SEQ ID NO: 77) | | |
| methicillin resistant mecC | mecC-R | ggccatatcctgaatctgctaataa (SEQ ID NO: 78) | | |
| exogenous internal control | IC-F | gcttcttgtggagctcgacaa (SEQ ID NO: 79) | | |
| exogenous internal control | IC-R | ccgtcagcaacttcgttttca (SEQ ID NO: 80) | | |
| pseudomonas aeruginosa | TL-P | ccttgacatgctgagaac (SEQ ID NO: 81) | FAM | MGB |
| escherichia coli | DC-P | aagggagtaaagttaatacc (SEQ ID NO: 82) | FAM | MGB |
| klebsiella pneumoniae | FK-P | taacctcatcgattgacg (SEQ ID NO: 83) | FAM | MGB |
| acinetobacter baumannii | BM-P | ccttgacatactagaaactt (SEQ ID NO: 84) | FAM | MGB |
| staphylococcus aureus | JP-P | tagagccttcccctttcg (SEQ ID NO: 85) | VIC | MGB |
| enterococcus faecium | SC-P | atagagcttcccctttcgg (SEQ ID NO: 86) | VIC | MGB |
| enterococcus faecalis | FC-P | agagctttccctttcgg (SEQ ID NO: 87) | VIC | MGB |
| enterobacter cloacae | YG-P | aaggtgttgtggttaataa (SEQ ID NO: 88) | VIC | MGB |
| candida albicans | BS-P | cctgttatcccaaycaaac (SEQ ID NO: 89) | ROX | MGB |
| candida glabrata | GH-P | actaccagcagatgcg (SEQ ID NO: 90) | ROX | MGB |
| candida parapsilosis | JPH-P | ttagtatoggaagaactca (SEQ ID NO: 91) | ROX | MGB |
| candida tropicalis | RD-P | cagtatgtattctttaacacgttg (SEQ ID NO: 92) | ROX | MGB |
| carbapenem resistant KPC | KPC-P | gccgctcgggctagac (SEQ ID NO: 93) | CY5 | MGB |
| carbapenem resistant NDM | NDM-P | gccggtcgcgctggc (SEQ ID NO: 94) | CY5 | BHQ2 |

TABLE 1-continued

| Name | Number | Sequence | 5' modification | 3' modification |
|---|---|---|---|---|
| carbapenem resistant OXA48 | OXA48-P | gatttgggcgtggttaagga (SEQ ID NO: 95) | CY5 | MGB |
| carbapenem resistant IMP | IMP-P | caagagtgatgcgtctc (SEQ ID NO: 96) | CY5 | MGB |
| vancomycin resistant vanA | vanA-P | cagcagaggagcgagg (SEQ ID NO: 97) | A425 | BHQ1 |
| vancomycin resistant vanB | vanB-P | agagaatacgaaactcg (SEQ ID NO: 98) | A425 | BHQ1 |
| vancomycin resistant vanM | vanM-P | tgaaccaatatacatcggaata (SEQ ID NO: 99) | A425 | BHQ1 |
| methicillin resistant mecA | mecA-P | tgttaaagaagatggtatgtgg (SEQ ID NO: 100) | CY5.5 | BHQ2 |
| methicillin resistant mecC | mecC-P | ccttttataaagcacaaatc (SEQ ID NO: 101) | CY5.5 | MGB |
| exogenous internal control | IC-P | cgcgacggatctacgtcacagcg (SEQ ID NO: 102) | CY7 | BHQ3 |

EXAMPLE 2

Digital PCR Amplification System

1. A single amplification system is shown in Table 2

TABLE 2

| Component | Concentration of storage solution (μM) | Volume (μL) |
|---|---|---|
| water | | 9.475 |
| 5 × Taq mix | | 3 |
| 50 × positioning dye | | 0.3 |
| F | 400 | 0.0375 |
| R | 400 | 0.0375 |
| P | 100 | 0.0375 |
| IC-F | 400 | 0.0375 |
| IC-R | 400 | 0.0375 |
| IC-P | 100 | 0.0375 |
| IC template | | 1 |
| Bacterium DNA/resistant gene | | 1 |
| total | | 15 |

2. A multiplex amplification system is shown in Table 3

TABLE 3

| Component | Concentration of storage solution (μM) | Volume (μL/test) |
|---|---|---|
| water | | 6.4375 |
| 5 × Taq mix | | 3 |
| UP1 | 100 | 0.0375 |
| UP2 | 100 | 0.0375 |
| UP3 | 100 | 0.0375 |
| UP4 | 100 | 0.0375 |
| UP5 | 100 | 0.0375 |
| UP6 | 100 | 0.0375 |
| UP7 | 100 | 0.0375 |
| TL-F | 400 | 0.0375 |
| TL-R | 400 | 0.0375 |
| TL-UP1 | 100 | 0.0375 |
| DC-F | 400 | 0.0375 |
| DC-R | 400 | 0.0375 |
| DC-UP1 | 100 | 0.0375 |
| FK-F | 400 | 0.0375 |
| FK-R | 400 | 0.0375 |
| FK-UP1 | 100 | 0.0375 |
| BM-F | 400 | 0.0375 |
| BM-R | 400 | 0.0375 |
| BM-UP1 | 100 | 0.0375 |
| JP = F | 400 | 0.0375 |
| JP-R | 400 | 0.0375 |
| JP-UP2 | 100 | 0.0375 |
| SC-F | 400 | 0.0375 |
| SC-R | 400 | 0.0375 |
| SC-UP2 | 100 | 0.0375 |
| FC-F | 400 | 0.0375 |
| FC-R | 400 | 0.0375 |
| FC-UP2 | 100 | 0.0375 |
| YG-F | 400 | 0.0375 |
| YG-R | 400 | 0.0375 |
| YG-UP2 | 100 | 0.0375 |
| BS-F | 400 | 0.0375 |
| BS-R | 400 | 0.0375 |
| BS-UP3 | 100 | 0.0375 |
| GH-F | 400 | 0.0375 |
| GH-R | 400 | 0.0375 |
| GH-UP3 | 100 | 0.0375 |
| JPH-F | 400 | 0.0375 |
| JPH-R | 400 | 0.0375 |
| JPH-UP3 | 100 | 0.0375 |
| RD-F | 400 | 0.0375 |
| RD-R | 400 | 0.0375 |
| RD-UP3 | 100 | 0.0375 |
| KPC-F | 400 | 0.0375 |
| KPC-R | 400 | 0.0375 |
| KPC-UP4 | 100 | 0.0375 |
| NDM-F | 400 | 0.0375 |
| NDM-R | 400 | 0.0375 |
| NDM-UP4 | 100 | 0.0375 |
| OXA48-F | 400 | 0.0375 |
| OXA48-R | 400 | 0.0375 |
| OXA48-UP4 | 100 | 0.0375 |
| IMP-F | 400 | 0.0375 |
| IMP-R | 400 | 0.0375 |
| IMP-UP4 | 100 | 0.0375 |

TABLE 3-continued

| Component | Concentration of storage solution (μM) | Volume (μL/test) |
|---|---|---|
| vanA-F | 400 | 0.0375 |
| vanA-R | 400 | 0.0375 |
| vanA-UP5 | 100 | 0.0375 |
| vanB-F | 400 | 0.0375 |
| vanB-R | 400 | 0.0375 |
| vanB-UP5 | 100 | 0.0375 |
| vanM-F | 400 | 0.0375 |
| vanM-R | 400 | 0.0375 |
| vanM-UP5 | 100 | 0.0375 |
| mecA-F | 400 | 0.0375 |
| mecA-R | 400 | 0.0375 |
| mecA-UP6 | 100 | 0.0375 |
| mecC-F | 400 | 0.0375 |
| mecC-R | 400 | 0.0375 |
| mecC-UP6 | 100 | 0.0375 |
| IC-F | 400 | 0.0375 |
| IC-R | 400 | 0.0375 |
| IC-UP7 | 100 | 0.0375 |
| IC template | | 1 |
| Bacterium DNA/resistant gene | | 1 |
| total | | 15 |

3. An Amplification Program

95° C. 5 min, (95° C. 15 s, 60° C. 1 min)×40

4. A Result Interpretation (1) A detection result of the single amplification system is shown in Table 4

TABLE 4

| | Sample | | | | | | |
|---|---|---|---|---|---|---|---|
| | A425 (copies)/μL | FAM (copies)/μL | VIC (copies)/μL | ROX (copies)/μL | CY5 (copies)/μL | CY5.5 (copies)/μL | CY7 (copies)/μL |
| pseudomonas aeruginosa | / | 108.44 | / | / | / | / | 258.64 |
| escherichia coli | / | 218.62 | / | / | / | / | 267.33 |
| klebsiella pneumoniae | / | 58.17 | / | / | / | / | 249.66 |
| acinetobacter baumannii | / | 333.19 | / | / | / | / | 263.55 |
| staphylococcus aureus | / | / | 1186.95 | / | / | / | 248.71 |
| enterococcus faecium | / | / | 2137.44 | / | / | / | 265.89 |
| enterococcus faecalis | / | / | 29.66 | / | / | / | 252.12 |
| enterobacter cloacae | / | / | 87.11 | / | / | / | 267.81 |
| candida albicans | / | / | / | 45.19 | / | / | 257.75 |
| candida glabrata | / | / | / | 86.77 | / | / | 249.46 |
| candida parapsilosis | / | / | / | 83.98 | / | / | 252.33 |
| candida tropicalis | / | / | / | 36.44 | / | / | 249.6 |
| carbapenem resistant KPC | / | / | / | / | 109.53 | / | 246.28 |
| carbapenem resistant NDM | / | / | / | / | 218.62 | / | 258.47 |
| carbapenem resistant OXA48 | / | / | / | / | 317.4 | / | 245.54 |
| carbapenem resistant IMP | / | / | / | / | 211.09 | / | 247.9 |
| vancomycin resistant vanA | 319.9 | / | / | / | / | / | 251.11 |
| vancomycin resistant vanB | 856.71 | / | / | / | / | / | 259.14 |
| vancomycin resistant vanM | 2365.47 | / | / | / | / | / | 246.77 |
| methicillin resistant mecA | / | / | / | / | / | 1166.22 | 248.83 |
| methicillin resistant mecC | / | / | / | / | / | 2312.89 | 264 |

(2) A detection result of the multiplex amplification system is shown in Table 5

TABLE 5

| | Sample | | | | | | |
|---|---|---|---|---|---|---|---|
| | A425 (copies)/μL | FAM (copies)/μL | VIC (copies)/μL | ROX (copies)/μL | CY5 (copies)/μL | CY5.5 (copies)/μL | CY7 (copies)/μL |
| pseudomonas aeruginosa | 0 | 124.16 | 0 | 0 | 0 | 0 | 248.66 |
| escherichia coli | 0 | 214.33 | 0 | 0 | 0 | 0 | 243.77 |
| klebsiella pneumoniae | 0 | 55.22 | 0 | 0 | 0 | 0 | 265.56 |
| acinetobacter baumannii | 0 | 324.5 | 0 | 0 | 0 | 0 | 249.35 |
| staphylococcus aureus | 0 | 0 | 1150.33 | 0 | 0 | 0 | 243.22 |
| enterococcus faecium | 0 | 0 | 2140.62 | 0 | 0 | 0 | 249.17 |
| enterococcus faecalis | 0 | 0 | 35.16 | 0 | 0 | 0 | 256.71 |
| enterobacter cloacae | 0 | 0 | 85.29 | 0 | 0 | 0 | 256.33 |
| candida albicans | 0 | 0 | 0 | 48.27 | 0 | 0 | 265.81 |
| candida glabrata | 0 | 0 | 0 | 85.66 | 0 | 0 | 268.66 |
| candida parapsilosis | 0 | 0 | 0 | 89.42 | 0 | 0 | 259.18 |
| candida tropicalis | 0 | 0 | 0 | 32.15 | 0 | 0 | 246.83 |
| carbapenem resistant KPC | 0 | 0 | 0 | 0 | 106.24 | 0 | 247.5 |
| carbapenem resistant NDM | 0 | 0 | 0 | 0 | 215.43 | 0 | 258.6 |
| carbapenem resistant OXA48 | 0 | 0 | 0 | 0 | 321.99 | 0 | 240.21 |
| carbapenem resistant IMP | 0 | 0 | 0 | 0 | 205.32 | 0 | 253.17 |
| vancomycin resistant vanA | 314.44 | 0 | 0 | 0 | 0 | 0 | 248.59 |
| vancomycin resistant vanB | 850.41 | 0 | 0 | 0 | 0 | 0 | 252.33 |
| vancomycin resistant vanM | 2377.82 | 0 | 0 | 0 | 0 | 0 | 242.59 |
| methicillin resistant mecA | 0 | 0 | 0 | 0 | 0 | 1145.54 | 262.13 |
| methicillin resistant mecC | 0 | 0 | 0 | 0 | 0 | 2320.17 | 247.7 |

The results showed that the *Pseudomonas aeruginosa, Escherichia coli, Klebsiella pneumoniae* and *Acinetobacter baumannii* only had detection values in FAM and CY7, and there was no detection value in other channels.

The *Staphylococcus aureus, Enterococcus faecium, Enterococcus faecalis* and *Enterobacter cloacae* only had detection values in VIC and CY7, and there was no detection value in other channels.

The *Candida albicans, Candida glabrata, Candida parapsilosis* and *Candida tropicalis* only had detection values in ROX and CY7, and there was no detection value in other channels.

The carbapenem resistant genes only had detection values in CY5 and CY7, and there was no detection value in other channels.

The vancomycin resistant genes only had detection values in A425 and CY7, and there was no detection value in other channels.

The methicillin resistant genes only had detection values in CY5.5 and CY7, and there was no detection value in other channels.

In summary, the primers and probes provided by the present application can accurately detect a simulated sample, and the detection results were fully consistent with an expectation, which indicated that an accuracy of the detection system was normal. The system for detecting a plurality of pathogenic microorganisms and resistant genes in the present application had specificity. The detection results of the two detection systems were basically consistent, which indicated that the multiplex detection system of the present application has stability.

The above are the preferred embodiments of the present application. It should be noted that, those skilled in the art can make several changes or modifications according without departing from the principles of the present application, which should be covered within the protection scope of the present application.

What is claimed is:

1. A universal probe, wherein, from 5' end to 3' end, the universal probe sequentially comprises: quenching group-fragment A-fluorophore-fragment B-C3;
   the fragment A has a nucleotide sequence selected from a group consisting of SEQ ID NO:1-7; and
   the fragment B has a nucleotide sequence selected from a group consisting of SEQ ID NO:8-14.

2. The universal probe according to claim 1, wherein, from 5' end to 3' end, the universal probe sequentially comprises one selected from a group consisting of:
   quenching group-fragment A having a nucleotide sequence of SEQ ID NO:1-fluorophore-fragment B-C3 having a nucleotide sequence of SEQ ID NO:8;
   quenching group-fragment A having a nucleotide sequence of SEQ ID NO:2-fluorophore-fragment B-C3 having a nucleotide sequence of SEQ ID NO:9;
   quenching group-fragment A having a nucleotide sequence of SEQ ID NO:3-fluorophore-fragment B-C3 having a nucleotide sequence of SEQ ID NO:10;
   quenching group-fragment A having a nucleotide sequence of SEQ ID NO:4-fluorophore-fragment B-C3 having a nucleotide sequence of SEQ ID NO:11;
   quenching group-fragment A having a nucleotide sequence of SEQ ID NO:5-fluorophore-fragment B-C3 having a nucleotide sequence of SEQ ID NO:12;
   quenching group-fragment A having a nucleotide sequence of SEQ ID NO:6-fluorophore-fragment B-C3 having a nucleotide sequence of SEQ ID NO:13; and
   quenching group-fragment A having a nucleotide sequence of SEQ ID NO:7-fluorophore-fragment B-C3 having a nucleotide sequence of SEQ ID NO:14.

3. The universal probe according to claim 1, wherein, the fluorophore is selected from a group consisting of FAM, VIC, ROX, CY5, A425, CY5.5 and CY7; and the quenching group is selected from a group consisting of BHQ1, BHQ2 and BHQ3.

4. A primer-probe set for detecting one selected from a group consisting of a pathogenic microorganism and a resistant gene, comprising the universal probe according to claim 1, a specific primer pair and a single-modified fluorescence-free probe, wherein the specific primer pair targets the pathogenic microorganism and the resistant gene.

5. The primer-probe set according to claim 4, wherein, a nucleotide sequence of the single-modified fluorescence-free probe is reversely complementary to the nucleotide sequence of the fragment B in the universal probe.

6. The primer-probe set according to claim 5, wherein, 3' end of the single-modified fluorescence-free probe is labeled with the quenching group.

7. The primer-probe set according to claim 6, wherein, the quenching group labeled at 3' end of the single-modified fluorescence-free probe is selected from MGB, BHQ1, BHQ2 and BHQ3.

8. The primer-probe set according to claim 4, wherein, the single-modified fluorescence-free probe has a nucleotide sequence selected from a group consisting of SEQ ID NO:15-36.

9. The primer-probe set according to claim 4, wherein,
   the pathogenic microorganism comprises one selected from a group consisting of *Pseudomonas aeruginosa, Escherichia coli, Klebsiella pneumoniae, Acinetobacter baumannii, Staphylococcus aureus, Enterococcus faecium, Enterococcus faecalis, Enterobacter cloacae, Candida albicans, Candida glabrata, Candida parapsilosis* and *Candida tropicalis*; and
   the resistant gene comprises one selected from a group consisting of carbapenem resistant KPC gene, carbapenem resistant NDM gene, carbapenem resistant OXA48 gene, carbapenem resistant IMP gene, vancomycin resistant vanA gene, vancomycin resistant vanB gene, vancomycin resistant vanM gene, methicillin resistant mecA gene and methicillin resistant mecC gene.

10. The primer-probe set according to claim 9, wherein,
    a primer pair targeting the *Pseudomonas aeruginosa* has a nucleotide sequence selected from a group consisting of SEQ ID NO:37-38;
    a primer pair targeting the *Escherichia coli* has a nucleotide sequence selected from a group consisting of SEQ ID NO:39-40;

a primer pair targeting the *Klebsiella pneumoniae* has a nucleotide sequence selected from a group consisting of SEQ ID NO:41-42;

a primer pair targeting the *Acinetobacter baumannii* has a nucleotide sequence selected from a group consisting of SEQ ID NO:43-44;

a primer pair targeting the *Staphylococcus aureus* has a nucleotide sequence selected from a group consisting of SEQ ID NO:45-46;

a primer pair targeting the *Enterococcus faecium* has a nucleotide sequence selected from a group consisting of SEQ ID NO:47-48;

a primer pair targeting the *Enterococcus faecalis* has a nucleotide sequence selected from a group consisting of SEQ ID NO:49-50;

a primer pair targeting the *Enterobacter cloacae* has a nucleotide sequence selected from a group consisting of SEQ ID NO:51-52;

a primer pair targeting the *Candida albicans* has a nucleotide sequence selected from a group consisting of SEQ ID NO:53-54;

a primer pair targeting the *Candida glabrata* has a nucleotide sequence selected from a group consisting of SEQ ID NO:55-56;

a primer pair targeting the *Candida parapsilosis* has a nucleotide sequence selected from a group consisting of SEQ ID NO:57-58;

a primer pair targeting the *Candida tropicalis* has a nucleotide sequence selected from a group consisting of SEQ ID NO:59-60;

a primer pair targeting the carbapenem resistant KPC gene has a nucleotide sequence selected from a group consisting of SEQ ID NO:61-62;

a primer pair targeting the carbapenem resistant NDM gene has a nucleotide sequence selected from a group consisting of SEQ ID NO:63-64;

a primer pair targeting the carbapenem resistant OXA48 gene has a nucleotide sequence selected from a group consisting of SEQ ID NO:65-66;

a primer pair targeting the carbapenem resistant IMP gene has a nucleotide sequence selected from a group consisting of SEQ ID NO:67-68;

a primer pair targeting the vancomycin resistant vanA gene has a nucleotide sequence selected from a group consisting of SEQ ID NO:69-70;

a primer pair targeting the vancomycin resistant vanB gene has a nucleotide sequence selected from a group consisting of SEQ ID NO:71-72;

a primer pair targeting the vancomycin resistant vanM gene has a nucleotide sequence selected from a group consisting of SEQ ID NO:73-74;

a primer pair targeting the methicillin resistant mecA gene has a nucleotide sequence selected from a group consisting of SEQ ID NO:75-76; and, a primer pair targeting the methicillin resistant mecC gene has a nucleotide sequence selected from a group consisting of SEQ ID NO:77-78.

11. A kit, comprising one selected from a group consisting of the universal probe described in claim 1 or a primer-probe set for detecting one selected from a group consisting of a pathogenic microorganism and a resistant gene, and an auxiliary agent or a carrier, wherein the primer-probe set for detecting one selected from a group consisting of a pathogenic microorganism and a resistant gene comprises the universal probe according to claim 1, a specific primer pair and a single-modified fluorescence-free probe, and the specific primer pair targets the pathogenic microorganism and the resistant gene.

\* \* \* \* \*